United States Patent [19]

Beachley, Jr.

[11] Patent Number: 4,621,147

[45] Date of Patent: Nov. 4, 1986

[54] NOVEL TRIVALENT ORGANOMETALLIC COMPOUNDS AND METHODS OF PREPARING SAME

[75] Inventor: Orville T. Beachley, Jr., Buffalo, N.Y.

[73] Assignee: State University of New York, Albany, N.Y.

[21] Appl. No.: 673,836

[22] Filed: Nov. 21, 1984

[51] Int. Cl.$^4$ ............................................. C07F 5/00
[52] U.S. Cl. ........................................................ 556/1
[58] Field of Search ........................ 260/448 A; 556/1

[56] References Cited

U.S. PATENT DOCUMENTS 4,101,568  7/1978  Malpass et al. ................. 260/448 A
4,170,604  10/1979  Malpass et al. ................. 260/448 A

OTHER PUBLICATIONS

Chemical Abstracts 91:202011h (1979).
Chemical Abstracts 65:3994e (1966).
Mole et al, Organoaluminum Compounds, Elsevier Publ. Co. N.Y., pp. 54, 88 & 89 (1972).
Nesmeyanov et al, Methods of Elemento-Organic Chem. North Holland Publ. Co., Amsterdam, vol. 1, pp. 386–387, 506, 507, 526–528, 398 and 450 (1967).

*Primary Examiner*—Helen M. S. Sneed
*Attorney, Agent, or Firm*—Omri M. Behr

[57]  ABSTRACT

In the manufacture of semiconductors it is desirable to make controlled deposits of certain phosphides or arsenides of trivalent metals such as gallium, indium and aluminum. There are provided novel neopentyl derivatives of these metals whose stability characteristics makes them ideally suited for the above purpose.

7 Claims, No Drawings

NOVEL TRIVALENT ORGANOMETALLIC COMPOUNDS AND METHODS OF PREPARING SAME

BACKGROUND OF THE INVENTION

In the conventional preparation of semiconductors a predetermined amount of extremely pure metal phosphide or arsenide are laid down on the substrate crystal. The accepted mode of carrying out this process is to charge predetermined amounts of phosphine or arsine into a stream of hydrogen together with the appropriate amount of an organometallic compound. The said mixed gas stream is passed through a furnace at a predetermined temperature, said furnace containing the crystal on which deposition is desired. At the predetermined temperature, an elimination reaction will take place whereby the organic portion of the organometallic is eliminated and replaced by phosphorus or arsenic as is appropriate. In order for this reaction to take place properly and efficiently the organometallic utilized must be sufficiently stable under the furnace conditions that it does not decompose per se and yet it must be sufficiently reactive to permit the elimination reaction to occur substantially instantaneously when the gas stream enters the heated furnace area.

The organometallic should also be comparatively simple to prepare and, desirably, *not* be pyrophoric. That is to say, that should it accidently come into contact with air due to process errors, it would not spontaneously inflame.

Heretofore, the organic group used in the synthesis of these compounds has been the methyl group. However, the metalomethyls of this group are extremely volatile and pyrophoric. This handling disadvantage makes it desirable to provide alternative compounds.

The ethyl, isopropyl and isobutyl derivatives decompose too readily at elevated temperatures to permit the elimination reaction to take place in the proper manner.

SUMMARY OF THE INVENTION

There are provided the trisneopentyl derivatives of gallium, indium and aluminum and the bisneopentyl aluminum hydride. The first three of these compounds have greater thermal stability, and longer shelf life than other metalo-organic compounds of these metals. They are easier to prepare at lower cost of synthesis than the previously known compounds and moreover, lack pyrophoric character.

Furthermore, these compounds have a sufficient level of volatility to permit them to be utilized in the gas phase synthesis of the corresponding phosphides or arsenides, a procedure which is useful in the manufacture of various semiconductors containing the said phosphides and arsenides.

The bisneopentyl aluminum hydride while stable at room temperatures decomposes at high temperature to provide high purity deposition of aluminum metal.

The novel trisneopentyl organometallic compounds of the present invention are readily simply prepared in accordance with general procedure. The corresponding metal chloride is dissolved in diethyl ether. Neopentyl magnesium halide is prepared in another diethyl ether solution in the conventional manner and the thus produced Grignard reagent slowly added to the metal trichloride solution. The reaction product is obtained as an ether solution from which the ether is removed.

The bisneopentyl aluminum hydride is prepared by reacting liquid aluminum trisneopentyl with ether-free lithium aluminum hydride and the product extracted with a hydrocarbon solvent from which the desired organometallic hydride is obtained by low temperature crystallization.

DESCRIPTION OF THE PREFERRED EMBODIMENTS

Freshly prepared (suitably sublimed) metal trihalide is dissolved in dry ethereal solvent. There may be utilized the chlorides, bromides and iodides of gallium, indium or aluminum. However, it is preferred to use the chloride of gallium, the iodide of indium and the bromide of aluminum. While any ether may be employed as a solvent, it is preferred from the point of view of expense and simplicity, to utilize diethyl ether.

A neopentyl Grignard reagent is prepared in the conventional manner by reacting purified neopentyl halide, suitably the chloride or bromide, preferably the chloride, with magnesium turnings in dry diethyl ether under an inert gas atmosphere.

A very substantial excess of Grignard is utilized. Stoichiometrically the reaction requires three moles of Grignard metal trihalide. It is preferred however to utilize between 3 and 10, suitably about 4 moles of Grignard per mole of metal trihalide.

The ethereal solution of the Grignard reagent is then slowly added to the metal trihalide ether solution at ambient temperature over a period of from about 15 to 25 minutes, suitably over a period of about 20 minutes under a dry inert atmosphere. Upon completion of addition the reaction mixture is stirred for a further 12 to about 24 hours again at ambient temperature.

As is not unusual in reactions of this type, a voluminous precipitate of magnesium halide is obtained which absorbs a very substantial amount of product in the form of the metal trialkyl etherate. It should further be noted that both the intermediate ethereate and the final metal trialkyl products are volatile. Hence, fractional distillation at this stage is not practical. The entire metal trialkyl etherate product therefore, is distilled under reduced pressure (typically at 0.01 mm of Hg) utilizing a bath temperature of about 125° C. into a side-arm flask, cooled to liquid nitrogen temperature (circa −196° C.). In order to obtain good yields, the distillation should be continued for from about 4 to about 7 hours. The solvent is then removed from the product by vacuum distillation (about 0.01 mm) at ambient temperature. The reaction product is then finally purified by vacuum distillation.

An alternate procedure is available for the synthesis of the trisneopentyl aluminum. In place of utilizing a Grignard reagent, there is utilized lithium neopentyl. The reaction is carried out in a saturated hydrocarbon solvent, suitably in pentane rather than in ether; however, the reaction conditions times and work-up are substantially similar to those pertaining to the Grignard reaction.

The trisneopentyl aluminum may be converted to the corresponding bisneopentyl aluminum hydride by direct reaction with lithium aluminum hydride. Reaction is carried out in a dry box under inert gas atmosphere, suitably under argon. The aluminum trisneopentyl is mixed with a small (circa 10%) excess of recrystallized lithium aluminum hydride and heated at between about 75° to about 100°, suitably about 90° C. for from about 6 to about 18, suitably for about 12 hours. The reaction mixture is cooled, dry pentane vacuum distilled onto the product which was then extracted several times with pentane and the resultant extract concentrated and cooled to dry ice temperature which causes crystallization of the desired product which was then isolated, suitably by filtration.

EXAMPLE I

Trisneopentylgallium

A flask charged with 9.578 g. (54.41 mmol) of freshly sublimed gallium trichloride dissolved in 250 ml. of dry diethyl ether (from sodium/benzophenone), was fitted with a condenser, mechanical stirrer and a pressure equalizing addition funnel. Under a cover of argon, 100 ml., 2.27M neopentyl magnesium chloride in diethyl ether solution (previously prepared from purified neopentyl chloride and magnesium turnings) was transferred to the addition funnel. The Grignard reagent was then added to the gallium trichloride solution over a period of 20 min. After the addtion was complete, the reaction mixture was stirred at room temperature for 18 hours. The stirrer, condenser and addition funnel were replaced by stoppers and Teflon vavle adapter. The diethyl ether was then removed by vacuum distillation at room temperature. The crude product, a trisneopentylgallium etherate mixture, was isolated by vacuum distillation at 125° C. into a side-arm flask (cooled to −196° C.) attached to the reaction flask by means of an 85° elbow. This distillation must be continued for approximately 5 hours. The diethyl ether was then removed from stirred, crude trisneopentyl gallium by simple vacuum distillation at room temperature for 1 hour. The product is finally purified by vacuum distillation in a short path still at 59.5° C. (0.01 mm, static vacuum). The yield of purified trisneopentyl gallium was 14.04 g (49.58 mmol, 91.1% based on gallium trichloride).

In accordance with the above procedure, but using the corresponding bromides or iodides in place of chlorides with either or both reagents, the same product is obtained.

Trisneopentyl gallium properties

Colorless liquid, slightly volatile at 20° C. Anal. (Schwarzkopf Microanalytical Laboratory) Calcd: C, 63.63; H, 11.75. Found: C, 63.64; H, 11.68. $^1$H NMR (C$_6$H$_6$ (7.13)δ) 1.06 (s, 27H, CCMe$_3$); 1.01 (s, 6H CH$_2$Ga). Cyroscopic molecular weight, benzene solution, formula weight 283.2 (calc. m, obs MW) 0.0770, 275; 0.0610, 291; 0.0510, 304. IR (pure liquid, cm$^{-1}$, relative intensity) 2950 vs, 2900 vs, 2860 vs, 2650 w, 1468 s, 1461 s, 1398 m, 1382 m, 1358 vs, 1229 s, 1132 m, 1095 m, 1031 m, 1006 s, 928 w, 909 w, 735 m, 703 m, 610 m, 591 m, 570 m, 460 sh, 450 m, 380 m, 310 m, 287 m. Trisneopentyl gallium is not pyrophoric but the compound is exceedingly sensitive to oxygen and water.

EXAMPLE II

Trisneopentylindium

A flask, charged with 29.13 g (58.3 mmol) of indium triiodide dissolved in 100 ml. of dry diethyl ether (from sodium/benzophenone), was fitted with a condenser, magnetic stir bar and a pressure equalizing addition funnel. Under a cover of argon, 100 ml., 2.32 M neopentyl magnesium chloride in diethyl ether solutin (previously prepared from purified neopentyl chloride and magnesium turnings) was transferred to the addition funnel. The Grignard reagent was then added to the indium triiodide solution over a period of 20 minutes. After the addition was complete, the reaction mixture was stirred at room temperature for 18 hours. The condenser and addition funnel were then replaced by a stopper and a Teflon valve adapter and the diethyl ether was removed by vacuum distillation at room temperature. The crude product, a trisneopentyl indium etherate mixture, was isolated by vacuum distillation at 110° C. into a side-arm flask (cooled to −196° C.) attached to the reaction flask by means of an 85° elbow. The distillation must be continued for approximately 8 hours. The diethyl ether was then removed from the crude trisneopentyl indium by simple vacuum distillation at room temperature for 12 hours. The product, a crystalline solid, is finally purified by vacuum sublimation at 30° C. with the receiving flask at −10° C. The yield of purified trisneopentyl indium was 17.7 g (53.9 mmol, 92.4% based on indium triiodide).

In accordance with the above procedure, but using the corresponding bromides or chlorides in place of iodides with either or both reagents, the same product is obtained.

Trisneopentyl indium properties

Colorless, crystalline solid. MP 54°-55° C. Sublimes at 27° C., 0.01 mm. Anal. Calc. (Schwarzkopf Microanalytical Laboratory) C, 54.88; H, 10.15. Found: C, 54.71; H, 10.15. Hydrolysis: 3.02 mol CMe$_4$/mol trisneopentyl indium. Cryoscopic molecular weight, benzene solution, formula weight 328.21 (calc. m, obs MW) 0.0940, 311.8; 0.0628, 331.5; 0.0472, 338.1. $^1$H NMR (C$_6$H$_6$ (7.13), δ) 1.11 (s, 27H, CCMe$_3$), 1.07 (s,6H InCH$_2$). IR (Nujol mull, cm$^{-1}$, relative intensity) bands of mulling agent omitted. 1379 s, 1371 s, 1228 vs, 1212 s, 1103 s, 1091 m, sh, 1007 s, 990 m, 922 w, 905 w, 800 vw, br, 734 m, 685 s, br, 570 s, 446 m, 372 m, 275 w, sh, 260 m, sh, 250 m, 245 m, sh, 240 m, sh. trisneopentyl indium is not pyrophoric but the compound is extremely sensitive to oxygen and water.

EXAMPLE III

Trisneopentylaluminum

A flask, charged with 11.26 g (42.44 mmol) of freshly sublimed aluminum tribromide dispersed with 100 ml. of dry pentane, was fitted with a condenser, mechanical stirrer and a powder addition funnel containing 9.89 g (126.7 mmol) of lithium neopentyl. The aluminum tribromide-hexane mixture was cooled to 0° C. and the lithium alkyl was then added to the aluminum tribromide over a period of 20 minutes. The reaction mixture was then refluxed for 3 hours. After the reaction was complete, the stirrer, condenser and addition funnel were replaced by a stopper, a Teflon valve adapter and a side-arm flask attached to the reaction flask by means of an 85° elbow. The pentane was then removed from the reaction mixture by vacuum distillation by heating the reaction flask at 110° with an oil bath while the side-arm flask was cooled at −196° C. Distillation must be continued for 8 hours in order to insure the complete removal of the product. The product is finally purified by vacuum distillation in a short path still at 55°-56° C. (0.01 mm, static vacuum). The yield of purified trisneopentyl aluminum was 8.38 g (34.9 mmol, 82.7% based on aluminum tribromide).

In accordance with the above procedure, but using the corresponding chlorides or iodides in place of bromides with either or both reagents, the same product is obtained.

Trisneopentyl aluminum properties

Colorless liquid, slightly volatile at 20° C. Anal. Calcd: C, 74.92; H, 13.86. Obs. 73.84, C 12.84 H. Hydrolysis 2.92 mol $CMe_4$/mol trisneopentyl aluminum. Cyroscopic molecular weight, benzene solution, formula weight 240.5. (Calcd. m, obs MW) 0.071, 227; 0.046, 237; 0.022, 267. $^1$H NMR ($C_6H_6$ (7.13)δ) 1.11 (s, 27H, $CCMe_3$), 0.56 (s, 6H, $CH_2Al$). IR (pure liquid, $cm^{-1}$, relative intensity) 2950 vs, 2860 vs, 1465 s, 1358 s, 1223 s, 1120 s, 1010 s, 990 m, 925 m, 910 m, 748 s, 695 s, 675 sh, 650 sh, 465 m, 390 m, 325 m. Trisneopentyl aluminum is not pyrophoric but the compound is exceedingly sensitive to oxygen and water.

EXAMPLE IV

Bisneopentylaluminum Hydride

A glass reaction vessel equipped with a Teflon high vacuum valve and a small stirring bar was charged with 3.02 g. (12.6 mmol) of trisneopentyl aluminum and 0.53 g. (13.9 mmol) of purified lithium aliminum hydride (recrystallized from ethyl but with all ethyl removed) in the dry box. After an inert-gas bubbler was attached to the Teflon valve adapter, the reaction mixture was heated at 90° C. for 12 hours. The reaction vessel was cooled and 25 ml. of dry pentane was vacuum distilled onto the product. The reaction vessel was then connected to a medium porosity frit and flask which was outfitted with a high vacuum Teflon valve. The reaction mixture was extracted three times with bisneopentylaluminum hydride being the only pentane soluble component. The resulting clear solution was then concentrated to a total volume of 7-10 ml. and was cooled to −78° C. to produce a crystalline product which was isolated by filtration. After removal of all pentane, 2.07 g. (12.2 mmol, 96.4% yield based on trisneopentyl aluminum of bisneopentylaluminum hydride was isolated. Alternatively, the product bisneopentylaluminum hydride can be isolated by sublimation at 50°-55° C. (0.01 mm).

Bisneopentylaluminum hydride properties

Colorless, crystalline solid which sublimes very slowly at room temperature (0.01 mm). MP 80°-82° C. Anal. by hydrolysis, Calc. 1 mol. $H_2$/mole bisneopentyl aluminum hydride; 2 mol $CMe_4$/mol bisneopentylaluminum hydride. Found: $H_2$, 0.996; $CMe_4$, 1.970. Cryoscopic molecular weight, benzene solution, formula weight 170.3 (calc. m, obs MW) 0.213, 442; 0.168, 409; 0.106, 419. $^1$H NMR ($C_6H_6$ (7.13)δ), 3.33, 3.13 (broad singlets, 1H, AlH), 1.13 (s, 18H, $CCMe_3$), 0.70, 0.67 (s, 4H, $AlCH_2$). The relative intensities of the two components for each of the Al-H and $AlCH_2$ lines are concentration dependent. IR (Nujol mull, $cm^{-1}$, relative intensity) bands due to mulling agent omitted. 2900 vs. 1770 s, 1460 s, 1355 s, 1223 s, 1120 m, 1093 m, 1035 w, 1010 m, 993 m, 928 w, 910 w, 820 w, 785 w, sh, 760 m, 740 w, sh, 705 m, 665 m, 505 m, 460 w, 398 w, 328 w, 296 m. This compound is exceedingly sensitive to oxygen and water.

I claim:

1. A metallo-organic compound of the structure: M $[CH_2C(CH_3)_3]_3$ wherein M is selected from the group consisting of Ga and In.

2. Trisneopentyl gallium, being a compound of claim 1.

3. Trisneopentyl indium, being a compound of claim 1.

4. A process of preparing a compound of claim 1, which comprises reacting $MX_3$ with neopentyl lithium in hydrocarbon solution, where X is iodo, bromo or chloro.

5. A process of claim 4 which comprises the further steps of removing the volatile portions of the reaction product and separating the desired trisneopentyl M therefrom.

6. A process of claim 5 wherein the volatiles are removed by distillation.

7. A process of claim 5 wherein the desired product is separated from the total volatiles by distillation.

* * * * *